United States Patent [19]

Spirig

[11] 4,227,415
[45] Oct. 14, 1980

[54] METHOD AND APPARATUS FOR TESTING SOLDERABILITY AND DE-SOLDERING WICKS

[76] Inventor: Ernst Spirig, P.O. Box 160, CH-8640 Rapperswil, Switzerland

[21] Appl. No.: 58,119

[22] Filed: Jul. 16, 1979

[30] Foreign Application Priority Data

Jun. 26, 1979 [GB] United Kingdom ............... 79/22181

[51] Int. Cl.³ ..................... G01M 19/00; G01N 33/00
[52] U.S. Cl. ................................................. 73/432 R
[58] Field of Search ............................... 73/432 R, 15

[56] References Cited
U.S. PATENT DOCUMENTS

| | | | |
|---|---|---|---|
| 3,859,290 | 12/1974 | Aitken et al. | 73/432 R |
| 3,901,008 | 8/1975 | Midgley | 73/432 R |

Primary Examiner—S. Clement Swisher
Attorney, Agent, or Firm—Lawrence E. Laubscher

[57] ABSTRACT

Apparatus and methods for testing the solderability of metal components and testing de-soldering wicks. The workpiece to be tested is lowered into a molten solder and upon contacting the solder an electrical circuit is completed to commence a timing cycle.

7 Claims, 2 Drawing Figures

METHOD AND APPARATUS FOR TESTING SOLDERABILITY AND DE-SOLDERING WICKS

BACKGROUND OF THE INVENTION

This invention relates to a method and apparatus for testing the solderability of a component or for testing de-soldering wicks.

Wicks or braids for de-soldering are known for example from my U.S. Pat. Nos. 4,081,575 and 4,078,714, my U.S. patent application Ser. No. 849,616 and Hood U.S. Pat. No. 3,627,191. Such wicks absorb, by capillary action, the unwanted solder which is melted during repair or exchange of components on printed circuit boards or terminal, for example. Thus, the end of the wick and a heated soldering iron are pressed onto the deposit of solder which is to be removed, and as this solder melts the de-soldering wick absorbs it.

Such use of a wick reduces the thermal stress on the printed circuit board. Thus, the cold wick acts as a heat sink and reduces the rate of rise of temperature. The maximum temperature reached is limited because the de-soldering wick absorbs the solder as soon as it melts: the quicker a wick absorbs, the less the temperature will rise above the melting point of the solder, and the smaller the amount of heat energy which flows into the area. The total of heat energy applied depends upon the temperature level and the time for which an elevated temperature is present and both these factors influence the reliability of the materials and components in the de-soldering area. A quick-acting wick is desirable as it reduces both the temperature level and the time for which an elevated temperature is present.

However, the problem arises as to how a wick user may compare the different makes of wick available to him. There are no special test procedures available to test the absorption rates of the different wicks. A proposal which I have made in the past to users is to employ a comparison dip test based on Military Standard 202E (Apr. 16, 1973), method 208C. This Mil-Standard is a test for solderability of components (for example solid terminals or wires) and involves dipping the component briefly into a bath of molten solder, and observing the percentage area of the component which remains coated with solder after the component has been lifted from the bath. FIG. 208-1 of Mil-Standard 202E suggests a dipping device or apparatus for carrying out the test. This device comprises a beam pivoted at a point intermediate its ends and a rotary cam acting on one end of the beam to firstly lower and then raise the other end of the beam, from which is suspended the component to be subjected to the solderability test.

This Mil-Standard dipping device suffers the disadvantage that the dipping depth is not taken into account automatically. It is to be noted that, as the solder in the bath is used, the solder level lowers and the depth to which components are immersed is accordingly reduced. Also, timings are controlled by the rotary cam. Variations in the testing times are only possible by changing the motor speed or changing the cam. Motor speed control would introduce a further factor to be controlled and measured closely, in order to ensure that conditions are equal for all tests in a comparitive series.

SUMMARY OF THE INVENTION

As seen from one aspect, in accordance with this invention there is provided testing apparatus for solderability and de-soldering wick tests, comprising holder means for holding a workpiece to be tested, drive means for driving the holder means selectively up and down, a molten solder bath into which the workpiece is dipped as the drive means drives the holder means first downwards and then upwards, an electrical circuit coupled to the workpiece and solder bath and completed through the workpiece and molten solder when the workpiece first touches the solder upon being driven downwards, and timing control means controlling the driving means and arranged to continue the downwards driving of the holder means for a predetermined interval after said circuit is completed, then to maintain the holder means stationary for a predetermined time period, and finally to raise the holder means so that the workpiece leaves the molten solder.

As seen from another aspect, in accordance with this invention there is provided a method of testing the solderability of a metal component, comprising attaching the component to a holder means positioned above a bath of molten solder, energising a drive means to drive the holder means downwards, responding to the completion of an electrical circuit through the component and molten solder and then continuing the downward drive of said holder means for a predetermined interval, thereafter maintaining the holder means and component stationary for a predetermined time period and finally energising said drive means to raise said component from the molten solder.

As seen from a further aspect, in accordance with this invention there is provided a method of testing a de-soldering wick, comprising attaching the wick to a holder means positioned above a bath of molten solder, energising a drive means to drive the holder means downwards, responding to the completion of an electrical circuit through the wick and molten solder and then continuing the downward drive of said holder means for a predetermined interval, thereafter maintaining the holder means and wick stationary for a predetermined time period and finally energising said drive means to raise said wick from the molten solder.

The apparatus and method in accordance with the invention enable an exactly controlled dipping depth and exact timings, to ensure that the comparative test results will be meaningful.

BRIEF DESCRIPTION OF THE DRAWINGS

An embodiment of this invention will now be described, by way of example only, with reference to the accompanying drawings, in which.

DESCRIPTION OF PREFERRED EMBODIMENT

Figure 1:
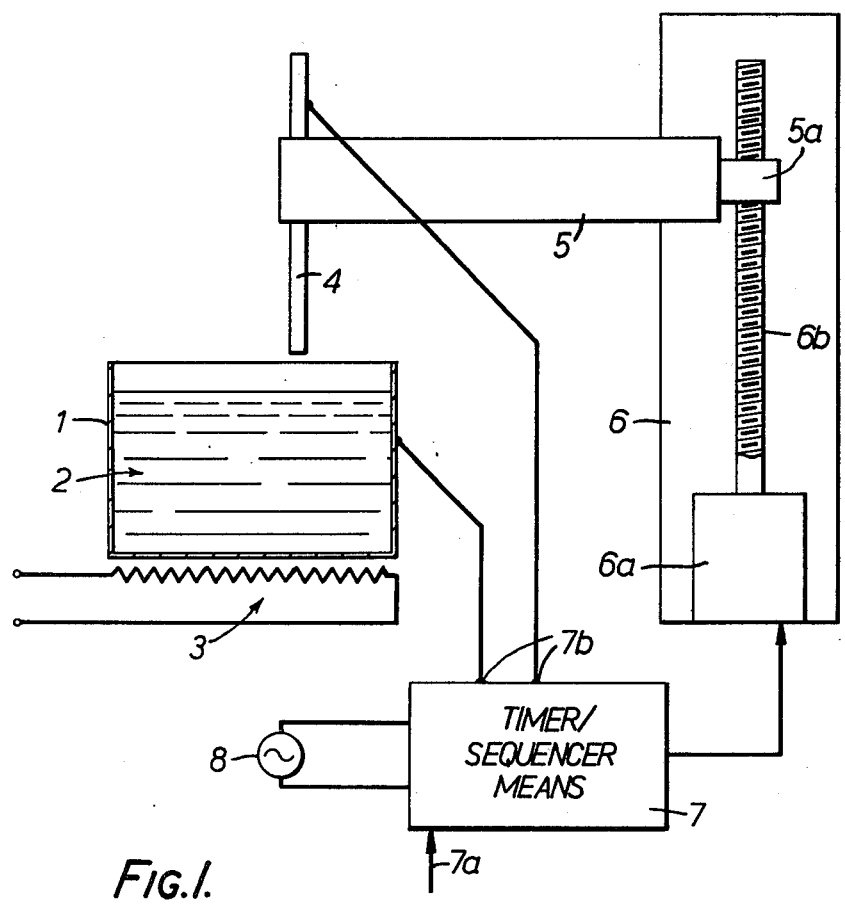
FIG. 1 is a schematic diagram of a testing apparatus in accordance with this invention.

Referring to FIG. 1 of the drawings, the testing apparatus comprises a molten solder bath 1, the solder 2 in which is heated to a thermostatically maintained temperature by electrical heating means 3. A workpiece, being a component to be tested for solderability, or a wick to be tested, is shown at 4 and is held, downwardly depending, in a holder means 5. Holder means 5 is driven vertically upwards and downwards by a drive means 6 which, in the example shown, comprises an electric motor 6a driving a screw-threaded shaft 6b on which is threaded a nut 5a carried non-rotatively by the holder means 5. A timing control means 7 is provided to control energisation of the motor 6a from an A.C. source 8, and comprises a "manual start" input 7a and inputs 7b connected respectively to the solder bath 1 and to the component or wick 4.

In operation, in response to a "manual start" at its input 7a, the timing control means 7 energises the drive means to drive the holder means downwards. When the component or wick 4 first contacts the solder, an electrical circuit is completed, through the solder and the component or wick 4, between the inputs 7b. The timing control means is arranged to drive the holder means downwards for a predetermined interval, or period of time $T_1$ (see FIG. 2), after this circuit is completed. Then the drive means is de-energised and the holder means and component or wick 4 are held stationary for a predetermined time period $T_2$, after which the timing control means energises the drive means to raise the holder means: a time $T_3$ elapses before the circuit is broken by the workpiece 4 under test lifting from the solder. Then the drive means continues to lift the holder means for a predetermined time period $T_4$ after the circuit is thus broken, to drive the workpiece 4 upwards a safe distance for cooling.

Figure 2:
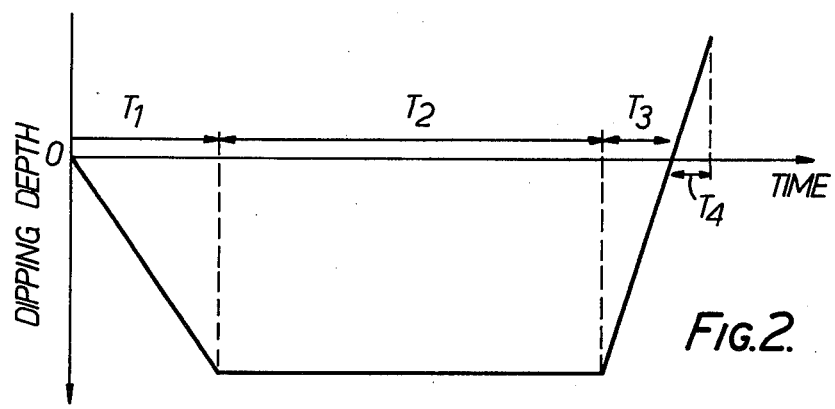
FIG. 2 is a timing chart for illustrating operation of the apparatus.

The downwards drive over the period $T_1$ is effected at constant speed and the upwards lift over periods $T_3$ and $T_4$ is also effected at constant speed, advantageously greater than the downwards speed over period $T_1$ (as shown in FIG. 2). Preferably, the total time $T_1+T_2+T_3$ is in the range of 1 to 3 seconds for testing de-soldering wicks. Reference might be made to the magazine "Insulation/Circuits", April 1978, pages 23-26 "Guidelines for Qualifying and Certifying Soldering Irons". Tables 2 and 3 list the tip temperatures and dwell times of different soldering irons at which a PC pad lifts. As temperature of the solder 2 in bath 1, a value should be established which corresponds to a soldering iron temperature. The Mil-Standard method 208C proposes 230° C.±5° C. (446° F.±9° F.). Table 2 suggests higher tip temperatures, from 560° F. up to 740° F. For wick testing a good compromise is about 650° F.(340° C.).

Wicks of different makes or construction but similar size (width by thickness) can be compared by the weight of solder absorbed within the established dipping time. Obviously the wick which does absorb in the same dipping time the most solder, will also in practice absorb the solder in less time, which means less excess temperature and less heat energy flow into desoldered area to influence reliability. Wick sizes available today from different makers are more or less identical (e.g. Spirig sizes 00, AA. AB BB and BC are equivalent to Hood sizes 1,2,3,4 and 5 , respectively. This test does not need any calculations and simply involves weighing before and after dipping, the difference being the amount of solder taken up by the wick.

I claim:

1. Testing apparatus for solderability and de-soldering wick tests, comprising holder means for holding a workpiece to be tested, drive means for driving the holder means selectively up and down, a molten solder bath into which the workpiece is dipped as the drive means drives the holder means first downwards and then upwards, an electrical circuit coupled to the workpiece and solder bath and completed through the workpiece and molten solder when the workpiece first touches the solder upon being driven downwards, and timing control means controlling the driving means and arranged to continue the downwards driving of the holder means for a predetermined interval after said circuit is completed, then to maintain the holder means stationary for a predetermined time period, and finally to raise the holder means so that the workpiece leaves the molten solder.

2. Testing apparatus as claimed in claim 1, in which the timing control means is arranged to drive the holder means downwards at a predetermined first speed and said interval is a period of time.

3. Testing apparatus as claimed in claim 2, in which the timing control means is arranged to drive the holder means upwards at a predetermined second, faster speed.

4. Testing apparatus as claimed in claim 1,2 or 3, in which the timing control means is responsive to said circuit being broken as the workpiece is raised from the solder and is arranged to drive said holder means upwards for a predetermined interval.

5. A method of testing the solderability of a metal component, comprising attaching the component to a holder means positioned above a bath of molten solder, energising a drive means to drive the holder means downwards, responding to the completion of an electrical circuit through the component and molten solder and then continuing the downward drive of said holder means for a predetermined interval, thereafter maintaining the holder means and component stationary for a predetermined time period and finally energising said drive means to raise said component from the molten solder.

6. A method of testing a de-soldering wick, comprising attaching the wick to a holder means positioned above a bath of molten solder, energising a drive means to drive the holder means downwards, responding to the completion of an electrical circuit through the wick and molten solder and then continuing the downward drive of said holder means for a predetermined interval, thereafter maintaining the holder means and wick stationary for a predetermined time period and finally energising said drive means to raise said wick from the molten solder.

7. A method as claimed in claim 6, comprising weighing the wick before and after dipping and determining the difference in weight.

* * * * *